(12) United States Patent
Gross et al.

(10) Patent No.: US 7,555,329 B2
(45) Date of Patent: Jun. 30, 2009

(54) METHOD AND APPARATUS FOR QUANTIFYING PHARYNGEAL RESIDUE

(75) Inventors: Roxann Diez Gross, Allison Park, PA (US); Richard S. Horne, Stafford, VA (US)

(73) Assignee: Department of Veterans Affairs, Baltimore, MD (US)

( * ) Notice: Subject to any disclaimer, the term of this patent is extended or adjusted under 35 U.S.C. 154(b) by 547 days.

(21) Appl. No.: 11/153,907

(22) Filed: Jun. 16, 2005

(65) Prior Publication Data
US 2005/0283064 A1 Dec. 22, 2005

Related U.S. Application Data

(60) Provisional application No. 60/580,382, filed on Jun. 18, 2004.

(51) Int. Cl.
*A61B 5/05* (2006.01)
(52) U.S. Cl. .................. 600/407; 600/408; 600/409; 600/410; 424/9.1; 424/9.41
(58) Field of Classification Search ......... 600/407–410, 600/437; 128/898; 424/9.1, 9.41
See application file for complete search history.

(56) References Cited

U.S. PATENT DOCUMENTS

| | | | | |
|---|---|---|---|---|
| 5,932,235 A | * | 8/1999 | Ninomiya et al. | 424/401 |
| 5,976,084 A | * | 11/1999 | Tymchuck | 600/300 |
| 6,461,589 B2 | * | 10/2002 | Robbins | 424/9.41 |
| 7,236,820 B2 | * | 6/2007 | Mabary et al. | 600/547 |
| 2008/0064990 A1 | * | 3/2008 | Blanco Guillermo et al. | 600/590 |

* cited by examiner

*Primary Examiner*—Long V Le
*Assistant Examiner*—Sanjay Cattungal
(74) *Attorney, Agent, or Firm*—Dykema Gossett PLLC

(57) ABSTRACT

A method and apparatus for quantifying pharyngeal residue and aspiration of a patient by x-ray imaging of the patient's head and neck to produce a baseline image, applying an initial volume of x-ray opaque solution to a patient by mouth; x-ray imaging the head and neck of the patient having received the solution before and after swallowing to produce respective second and third images; and calculating a ratio of the pharyngeal residue volume to the initial volume to determine the proportion of the swallowed bolus that remain in the pharyngeal recesses; and calculating a ratio of the material entering the trachea to the known initial volume to determine the proportion of the swallowed bolus that has been aspirated; and if the volume of the original bolus is known, calculating the actual volume of the pharyngeal residue and aspiration. The apparatus includes a suitably programmed computer and an x-ray imaging system to collect image data.

5 Claims, 11 Drawing Sheets

| Number | Date | Solution | AIR | Initial Vol | Residue Vol |
|---|---|---|---|---|---|
| 1 | 6/9/2005 | Thin Liquid | 0.38 | 10.00 | 3.78 |
| 2 | 6/9/2005 | Thin Liquid | 0.04 | 10.00 | 0.38 |

Fig. 10

METHOD AND APPARATUS FOR QUANTIFYING PHARYNGEAL RESIDUE

RELATED APPLICATION

This application is related to Provisional Patent Application Ser. No. 60/580,382 filed Jun. 18, 2004, teachings of which are incorporated herein by reference.

BACKGROUND OF THE INVENTION

The invention pertains to method and apparatus employing a computer program for quantifying pharyngeal residue and aspiration after swallowing observed in digital fluoroscopic images. In particular, the invention performs to a method and apparatus for the valid and reliable quantification of pharyngeal residue and aspiration so that comparisons can be made between experimental conditions and disorder groups.

To date, clinicians and researchers in the area of swallowing disorders have not been able to validly or reliably quantify pharyngeal residue or aspiration after swallowing. Prior methods are subjective and thus unreliable as to how much residue remained in the pharynx or how much of the bolus entered the trachea (prandial aspiration). This limitation has prevented researchers and clinicians from making accurate measurements of an abnormal condition where food and liquid remain in the neck after swallowing.

For example, it is not known how much pharyngeal residue is clinically significant, or if one location of residue (i.e. valleculae) verses another (i.e. pyriform sinuses) places a person at greater risk for aspiration or reduced nutrition. It is also unknown as to how much aspiration places a patient at risk for pulmonary complications and aspiration pneumonia.

SUMMARY OF THE INVENTION

The present invention employs a software program for converting images into quantifiable volumes that allow for the determination the amount of material remaining in the pharynx and the amount of material aspirated. The program will enable further research that has not been possible to date.

The ability to accurately and reliably quantify pharyngeal residue and aspiration will advance clinical research and practice by allowing for quantitative comparisons between treatments and disorder groups. Additionally it will allow for the development of operational definitions for mild, moderate, severe amounts of pharyngeal residue and aspiration.

BRIEF DESCRIPTION OF THE DRAWINGS

FIGS. 1-10 are screen images displayed at the workstation of the program operator, including images of the head and neck of the patient and dialog boxes displayed during operation of the program;

DESCRIPTION OF THE INVENTION

Figure 1:
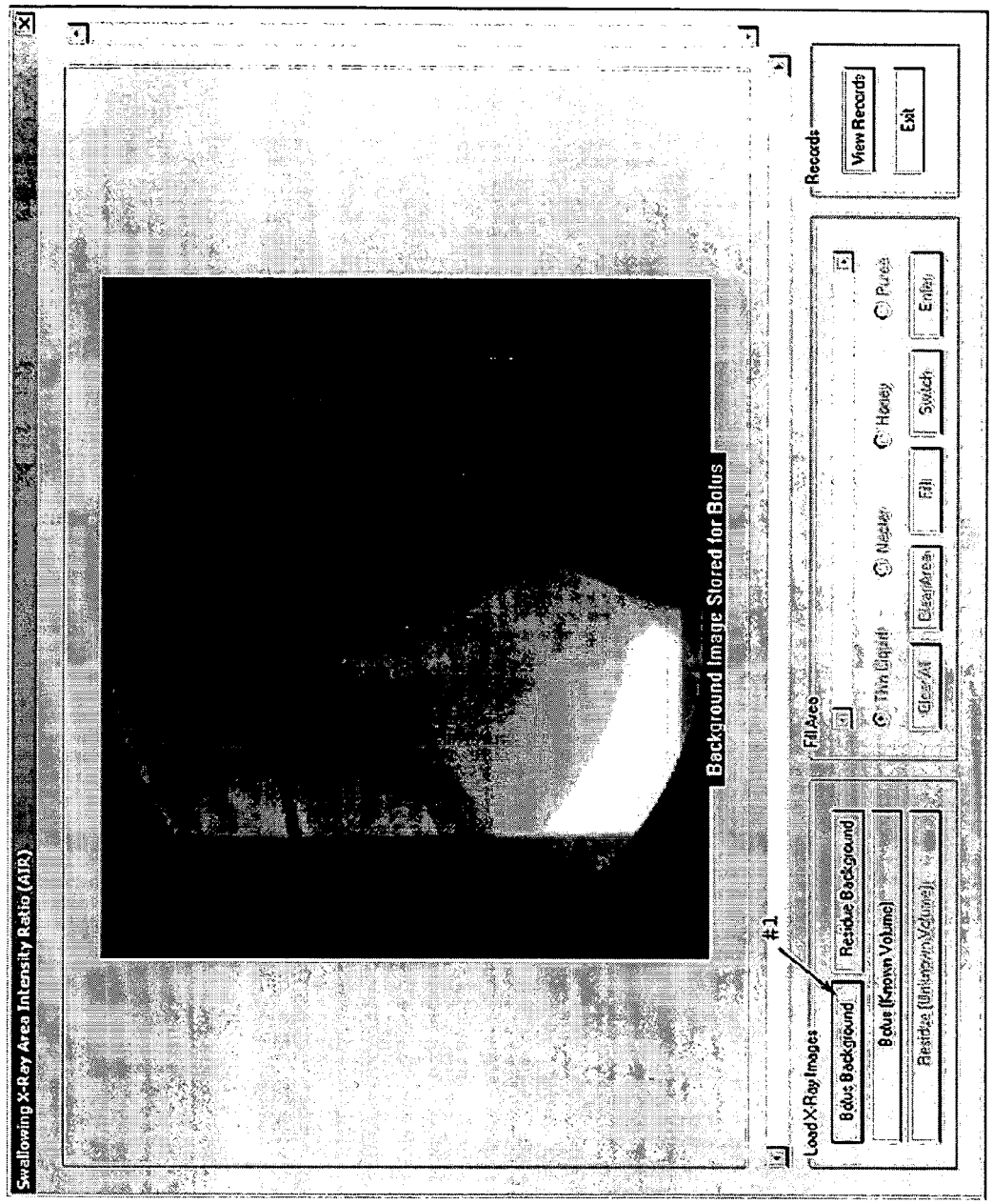

The invention is a program that utilizes pixel intensities in bolus and residue image areas of a patient X-Ray for the purpose of quantifying pharyngeal residue and aspiration. Baseline images of the head and neck and a pre-swallow digital image of a bolus are compared to a post-swallow digital image of residue and aspiration. Based upon the physics of X-Ray imaging, the program calculates the ratio of the volume of the residue and aspiration to the volume of the original bolus. These ratios are then a good indication of the patient's swallowing efficiency. If the volume of the original bolus is known, the volumes of the pharyngeal residue and aspiration may also be calculated from these ratios.

Software Description and Operation

Area Intensity Ratio (AIR) is a Windows ™ based computer program that utilizes pixel intensities in the bolus and residue image areas of a patient X-Ray for the purpose of quantifying pharyngeal residua and aspiration. With this program, baseline images of the head and neck and a pre-swallow digital image of a bolus are compared to post-swallow digital images of residue and aspiration. Based upon the physics of X-Ray imaging, the program then calculates the ratios of the volume of the residue and aspiration to the volume of the original bolus. If the original bolus volume is known, then the residue volume and aspiration volume is also computed from these ratios.

Physics of X-Ray Imaging

At the imaging display surface of an X-Ray device such as a fluoroscope, the pixel intensity $I_1$ resulting from the X-Ray beam passing through a patient is given by the formula.

$$I_1 = \alpha I_0 \exp(-\mu_1 x_1)$$

Where $I_0$ is the source X-Ray intensity, $\mu_1$ is the X-Ray attenuation coefficient of the patient's body, $x_1$ is the patient's body thickness, and $\alpha$ is a constant proportionality factor that relates pixel intensity to X-Ray beam intensity reaching the imaging device.

If an X-Ray opaque bolus solution is introduced into the path of the X-Rays. The image pixel intensity then becomes $$I_2 = \alpha I_0 \exp(-\mu_1 x_1 - \mu_2 x_2)$$

Where $x_2$ is the bolus thickness, and $\mu_2$ is the bolus X-Ray attenuation coefficient.

The thickness of the bolus at the point at which the X-Ray beam passed through can then be calculated by logarithmic subtraction according to:

$$ln(I_1) - ln(I_2) = [ln(\alpha I_0) - \mu_1 x_1] - [ln(\alpha I_0) - \mu_1 x_1 - \mu_2 x_2] \\ = \mu_2 x_2 \qquad (1)$$

$$x_2 = k\,[ln(I_1) - ln(I_2)] \text{ and}$$

$$k = 1/\mu_2$$

where k is a constant proportionality factor determined by the X-Ray attenuation coefficient of the bolus.

In other words, the thickness of the bolus at any point is proportional to the difference in the logarithms of image pixel intensity without and with the bolus present.

Equation 1 provides a means of calculating the relative volumes of a bolus before swallowing and the residue after swallowing. If the physical cross sectional area of the patient's body represented by each pixel is C, then the volume of the bolus measured from the X-Ray is set forth below:

$$V_b = ck \sum_{bolus} [\ln(I_{b1}) - \ln(I_{b2})] \qquad (2)$$

Where $I_{b2}$ ranges over all pixels in the bolus image and $I_{b1}$ is the corresponding pixel intensity from the patient's X-Ray at the same locations without the bolus present.

Likewise, the volume of the residue can be measured from the X-Ray as set forth below:

$$V_r = ck \sum_{residue} [\ln(I_{r1}) - \ln(I_{r2})] \quad (3)$$

Where $I_{r2}$ is the pixel intensity over all pixels in the residue image, and (2)

$I_{r1}$ is the corresponding pixel intensity from the patient's X-Ray at the same locations without the residue present.

The ratio of residue volume to bolus volume is then as set forth below:

$$R_{res} = \frac{V_r}{V_b} = \sum_{residue}[\ln(I_{r1}) - \ln(I_{r2})] / \sum_{bolus}[\ln(I_{b1}) - \ln(I_{b2})] \quad (4)$$

In order to calculate these sums and the ratio using the computer, baseline images of the patient's head and neck are required for summation of the $I_{r1}$ and $I_{b1}$ pixel values; an image of the head and neck with complete bolus is required for summation of the $I_{b2}$ pixel values; and an image of the head and neck with swallowing residue is required for summation of the $I_{r2}$ pixel values.

The function of the computer program then is to individually read and display the three required X-Ray images, and to provide graphical tools that allow the operator to mark all pixels contained in the bolus area of the image and all pixels contained in the residue area of the image. The program then calculates the logarithmic pixel intensity sums and the ratio of residual volume to original bolus volume.

It is also possible to calibrate the program for direct measurement of residual volume. If the initial bolus volume is precisely known, then the constant value of ck can be derived from Equation 2 and applied to Equation 3 to obtain a direct measurement of residue volume.

Program Operation

The X-Ray images used here are all digital image files (Windows bitmap or JPEG) taken using a fluoroscope and the Kay PENTAX Digital Swallowing Workstation. Other sources of digital X-Ray images may also be used.

Step 1: After starting the computer program, the operator chooses Bolus Background and selects a background X-Ray image of the patient's head and neck without the bolus present. (FIG. 1)

Depending on the circumstances, a separate background image for comparison with the residue image may be beneficial. For example, if there is a noticeable difference in the position of the patient's head between the time of the bolus image and the residue image, a separate residue background image that matches the patient's head position is advisable. The residue background image can be loaded here by clicking the Residue Background button. If a separate residue background image is not loaded, the program will use the single bolus background image for all calculations.

Figure 2:
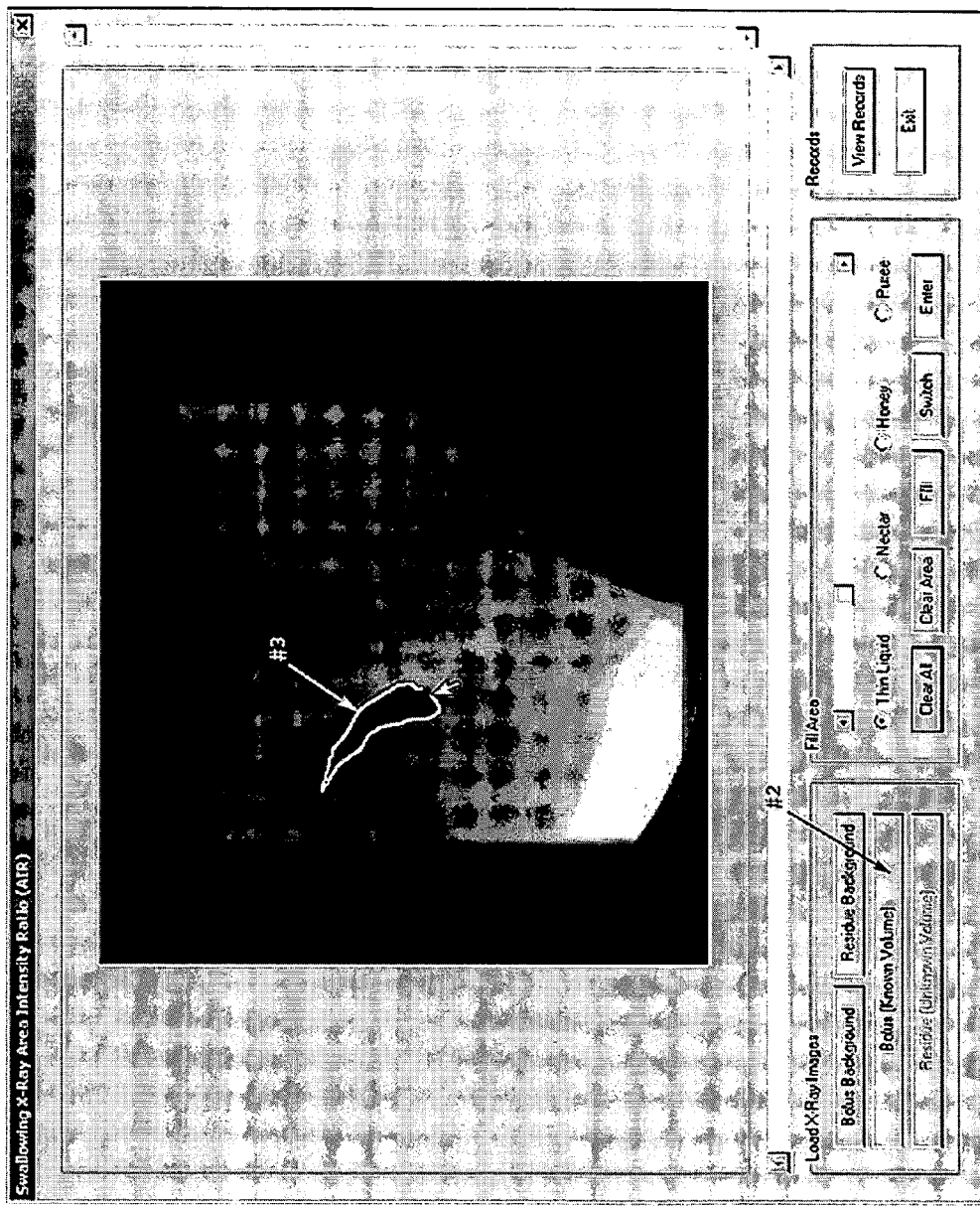

Step 2: The operator loads the bolus X-Ray image by clicking Bolus (Known Volume) and selecting an image of the patient's head and neck showing the full volume of the bolus in the early stages of swallowing. It is important to select an image here that shows the complete bolus since the pixel area of the bolus in this image will be compared with that of the residue image to determine the residue percentage. (FIG. 2)

Step 3: The operator outlines the area of the bolus using the mouse. Outlining may be performed by holding down the CTRL key and clicking and dragging using the left mouse.

Figure 3:

Step 4: After manually outlining the closed area of the bolus image, the operator clicks the Fill button and then clicks again with the mouse in the interior of bolus area. The program will then automatically fill the bolus image area on the X-Ray. (FIG. 3)

Figure 4:
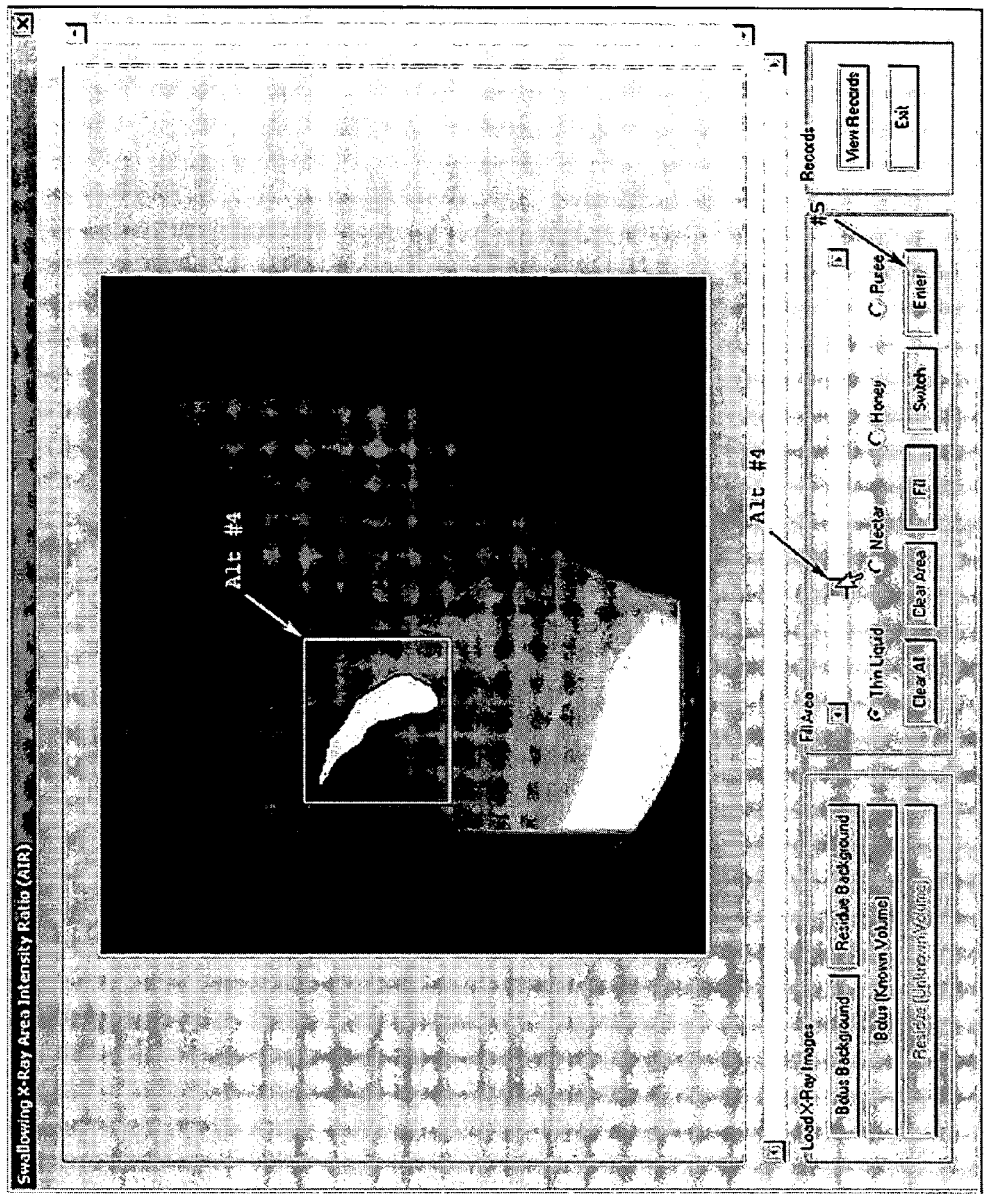

Alternative Step 4: An alternative to manually outlining of the bolus image is available. To use this method, the operator drags a rectangular box around the bolus image using the mouse and then moves the Fill Area horizontal slider to the right to automatically fill the darkest areas of the enclosed image. (FIG. 4)

Step 5: The Enter button is clicked to record the bolus image area and log pixel intensity summation in memory.

Figure 5:
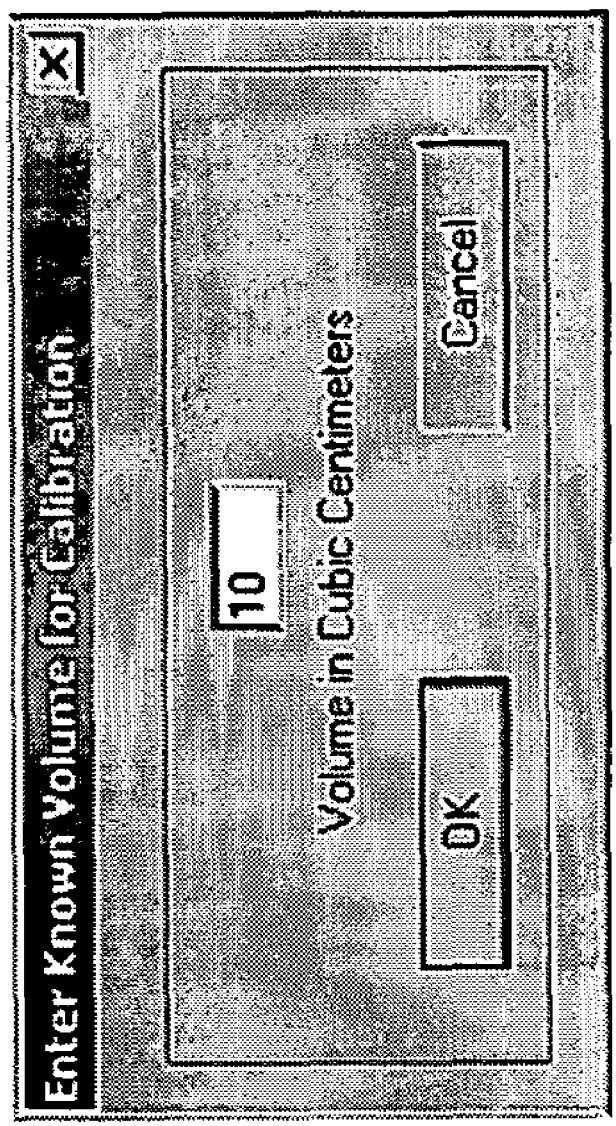

Step 6: At this point, the program will prompt the operator to enter the known volume of the bolus, e.g. 10 cc, (FIG. 5). If the initial bolus volume is known, the program calculates the actual residue volume, and reports it in appropriate units, e.g. cc s, from the residue to bolus volume ratio. If the bolus volume is unknown, a value of zero is entered here, and, no volume will be reported, only the residue to bolus volume ratio will be calculated.

It should be understood that during spontaneous eating and drinking, such as cup or straw drinking, the size of the bolus is not known. In persons with swallowing disorders, it is often not practical to control the bolus. The present invention handles this problem by looking at the images of the patient before and after swallowing in order to calculate the ratio of what was swallowed compared with what was introduced. This ratio does not depend on information as to the volume of the bolus introduced, but only the relative difference or percentage before and after swallowing. For example, the patient may swallow 50% of the bolus volume introduced. Even though it does not quantify volume, this percentage is a reliable measure of swallowing efficiency.

Figure 6:
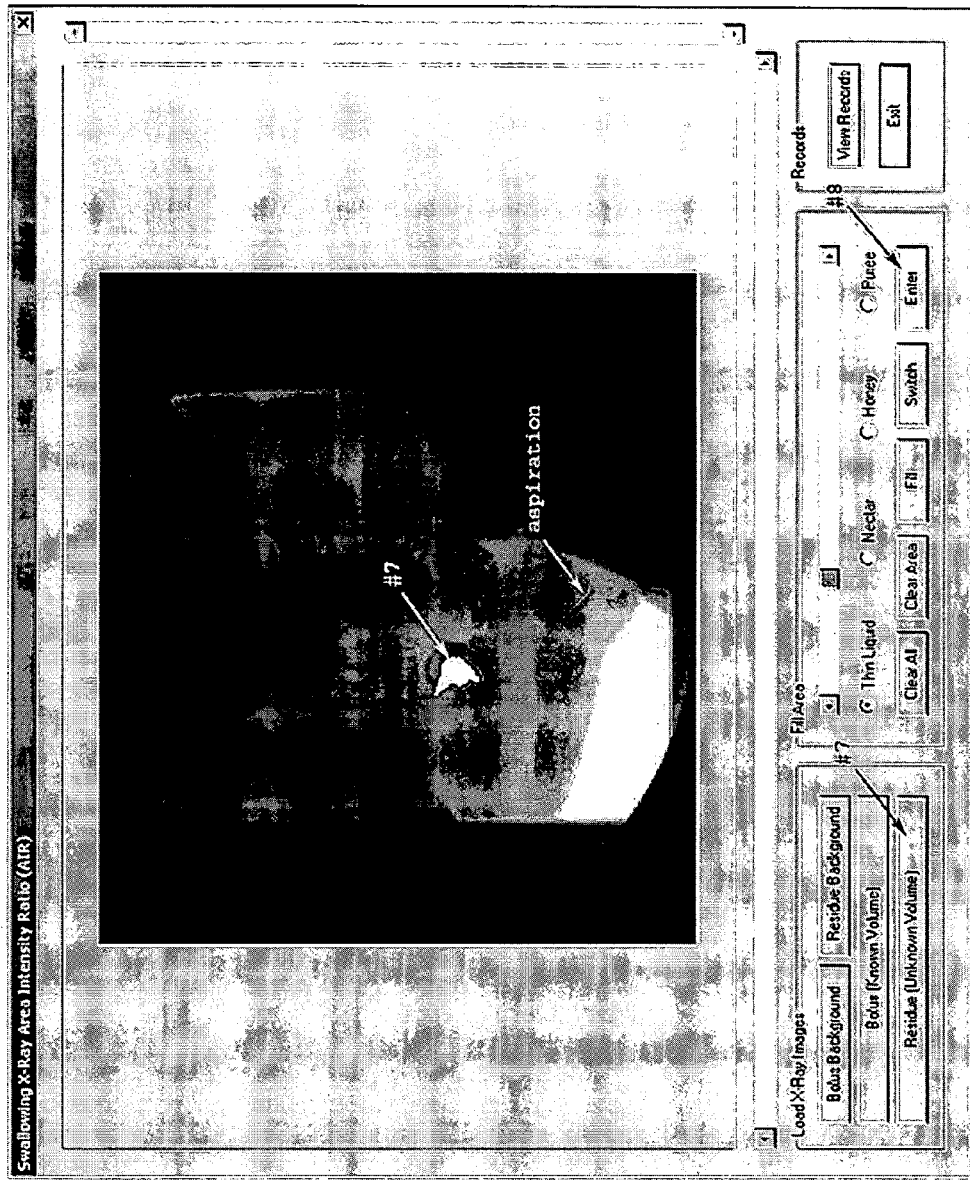

Step 7: Next the operator loads the residue image by clicking Residue (Unknown Volume). (FIG. 6) The residue image area is then filled using either image outlining or automatic filling as described previously for the bolus in Steps 3 and 4. It should be noted that this image also shows evidence of aspirated material in the trachea. See Step 10 regarding aspiration.

Step 8: The Enter button is clicked to record the residue image area and log pixel intensity summation in memory. The program will then compute and display the estimated residue volume (if available) and ratio of residue volume to bolus volume. Only the volume ratio estimate will be available here if the original bolus volume is unknown in Step 6.

Figure 7:
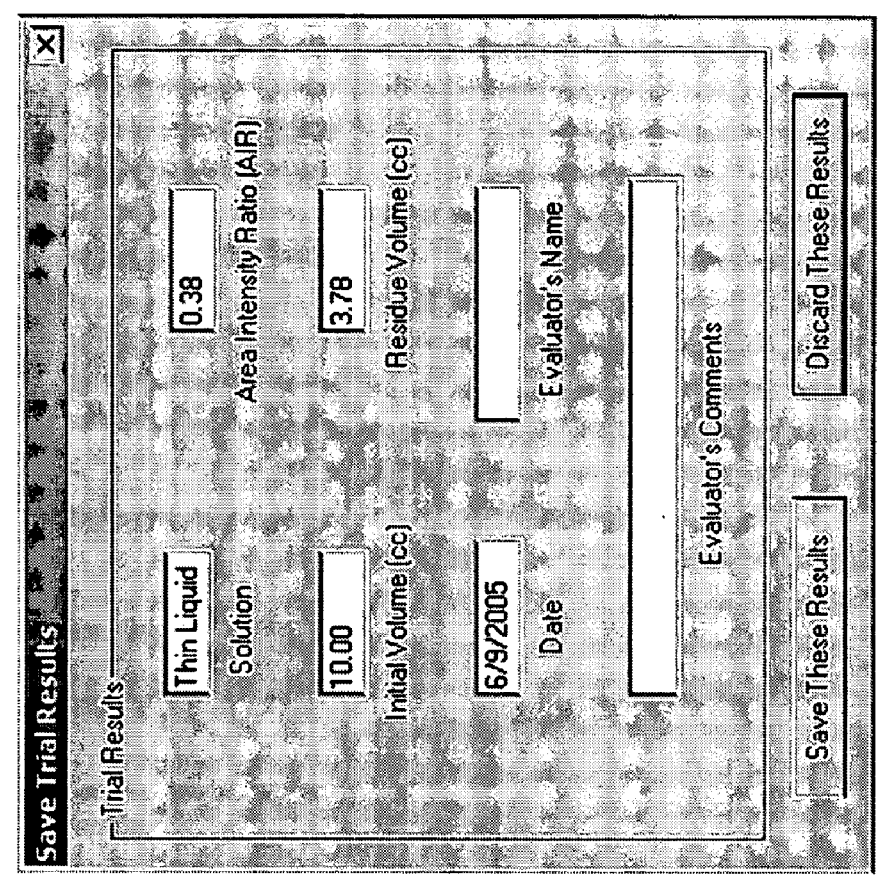

Step 9: Clicking the Save These Results button from the display (FIG. 7) will save all information about this measurement as well as the graphics image files used in the evaluation into a database folder in the AIR program directory on the host computer.

Figure 8:
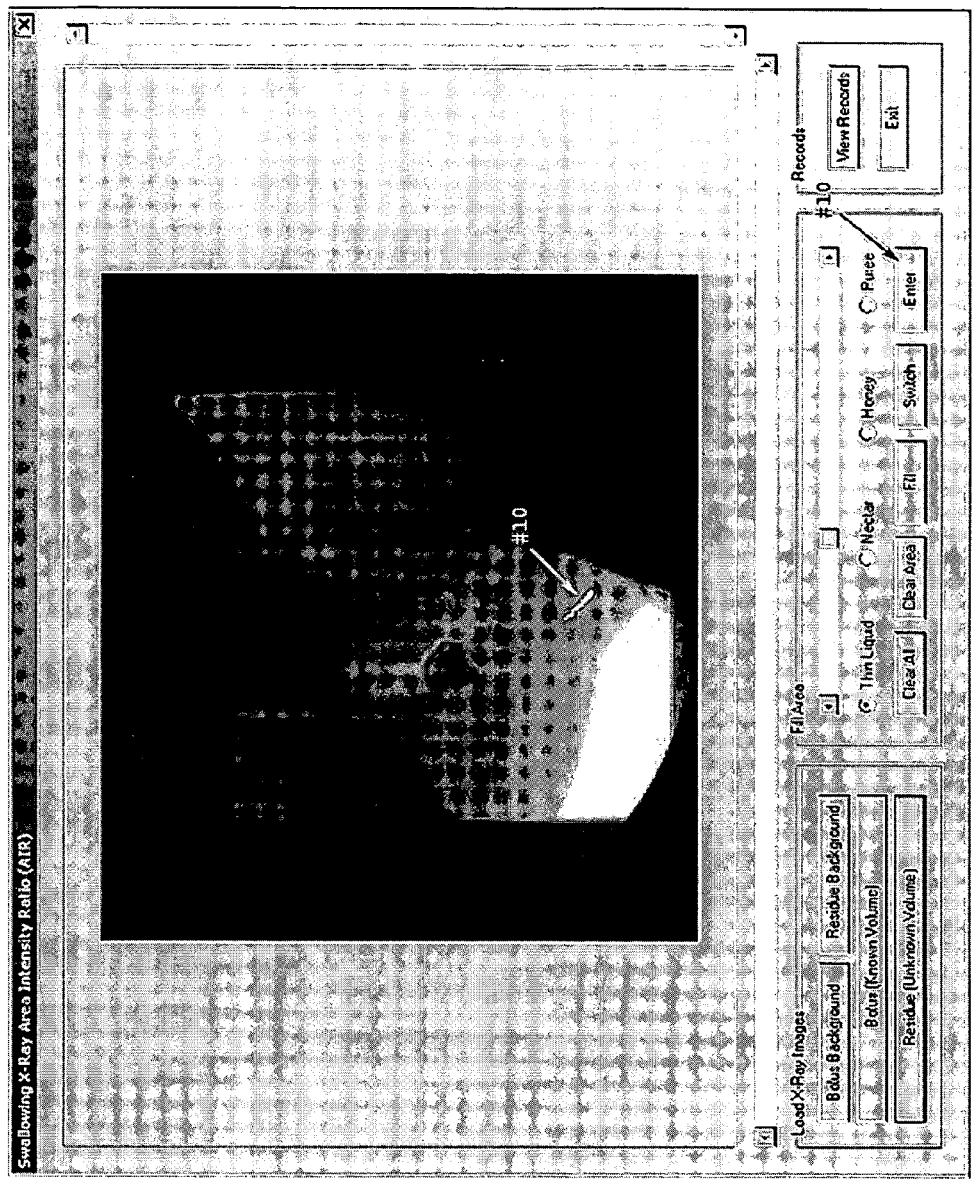

Step 10 (Aspiration): If aspiration is observed in the swallowing X-Ray images, it may also be quantified by repeating the procedures described for the bolus in Steps 2-9 using an image that captures the aspirated material while it is in the trachea. (FIG. 8) In the example shown, the image area of the aspirated material has been filled. Clicking the Enter button will then compute and display the estimated aspiration.

Reviewing Stored Records

Figure 9:
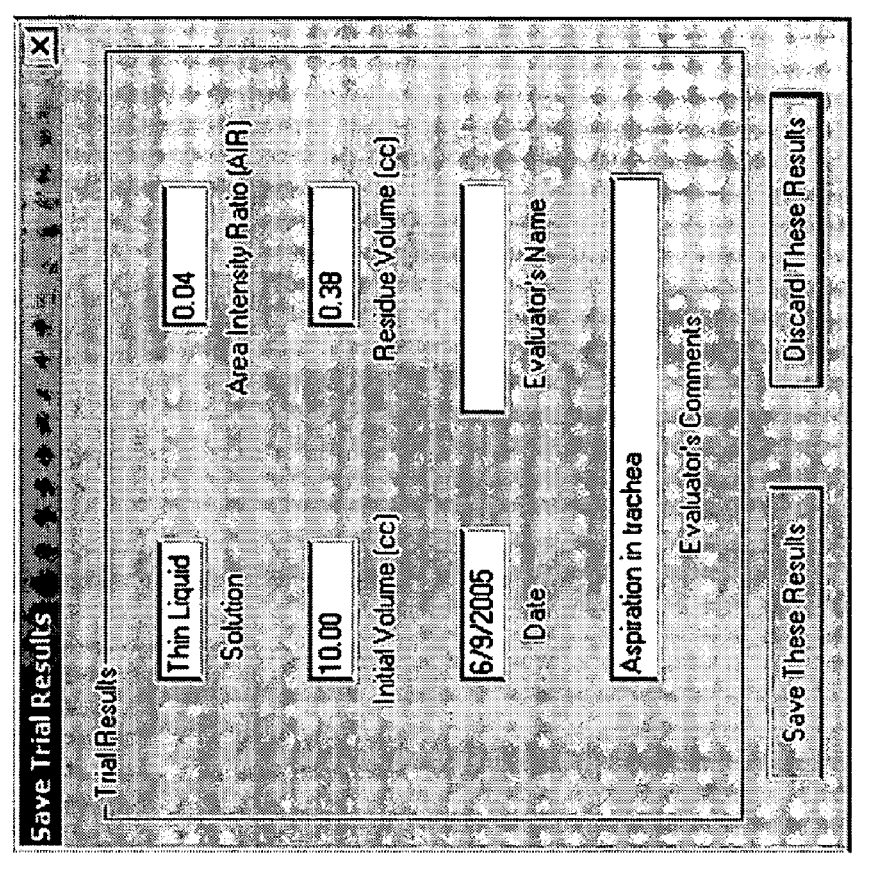

Clicking the View Records button will bring up the AIR Records window for examination or printing of stored measurements. (FIG. 9)

Controls are also provided for exporting or saving collected records to a database file folder and adding records from a previously saved database file folder. These controls provide the ability to establish separate database storage for different groups of patients, for example, or to keep separate records of several ongoing trials, e.g. Save Trail Results. (FIG. 10)

Other Considerations

It is important to measurement accuracy that the X-Ray equipment be adjusted to provide the maximum possible dynamic range (shades of gray) in the images used. The program depends on detecting differences in image pixel intensity resulting from the physical shape and thickness of the bolus and residual matter. Usually this will mean setting the contrast of the X-Ray image to a relatively low value so that variation in intensity can be observed across all areas of the image. If the contrast of the X-Ray image is set very high, the dark areas of the image will all be filled at minimum intensity (black) which may hamper the ability of the program to detect variations in the shape of the bolus and the residual material. The contrast may be adjusted for enhanced measurements. However, adjustments of this sort are within the skill level of program operators It should be understood that all measurements of a particular sample should be taken at the same image contrast level so that the measurements are consistent. Under such conditions, the relative difference among the measurements will be an indicator of the residual material in the sample.

Figure 11:
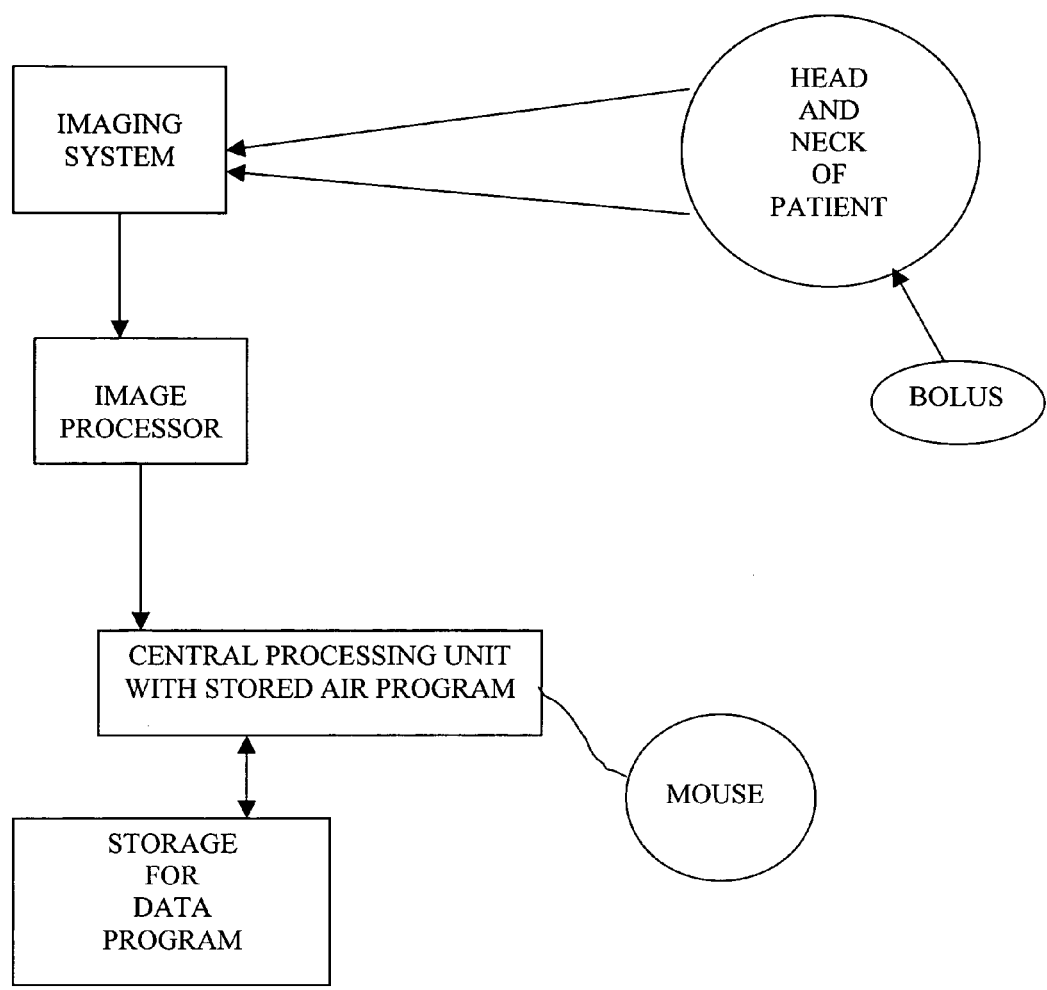
FIG. 11 is a schematic block diagram of a system for collecting and analyzing data for determining pharangeal residue in accordance with the invention.

Apparatus for performing the present invention includes an x-ray imaging device for producing digital or analog images of the head and neck of a patient; an image processing unit processes the images into a suitable digital format for use in the computer coupled thereto. The computer is suitably programmed with the AIR program to perform the process steps described above and employs a storage means for storing the images; and means for outlining and analyzing pixel data derived from the digital images. The operator of the system performs the steps in the sequence suggested for outlining the areas of the images to be analyzed. The operator may use the computer mouse or other suitable tool to outline the image of the bolus before and after swallowing, and the image of the trachea to determine what actually entered it in order to estimate aspirated amounts. A schematic block diagram of the system is illustrated generally in FIG. 11.

While there has been described what at present is considered to be an exemplary embodiment of the invention, it will be apparent to one of ordinary skill in the art that various changes and modifications may be made therein; and it is intended in the appended claims to cover such changes and modifications that fall within the scope of the claims.

The invention claimed is:

1. A method for quantifying pharyngeal residue and aspiration of a patient comprising the steps of: x-ray imaging the head and neck of the patient to produce a baseline image; administering an initial volume of x-ray opaque solution to a patient by mouth; x-ray imaging the head and neck of the patient having received the solution before swallowing to produce a second image; x-ray imaging the head and neck of the patient after swallowing to produce a third image; and calculating a ratio of the pharyngeal residue volume to the initial volume to determine the proportion of the swallowed bolus that remained in pharyngeal recesses of the patent; calculating a ratio of the volume of material entering the trachea to the initial volume to determine the proportion of the swallowed bolus that has been aspirated; calculating the actual volumes of the pharyngeal residue and aspiration.

2. The method of claim 1 further comprising: loading the baseline image, the second image and the third image into a computer; displaying the baseline image and the second and third images; outlining the bolus volume in the second image and the pharyngeal residue volume in the third image; recording the image areas; entering the known volume; comparing the image areas; computing the pharyngeal residue ratio from the measured image area and intensity in the first and second images as compared to the baseline image; and computing the pharyngeal residue volume as the product of the bolus volume and the calculated residue ratio.

3. The method of claim 2 further comprising: outlining the bolus volume in the second image and the volume of material entering the trachea in the third image; recording the image areas; entering the known volume; comparing the image areas; computing the aspiration residue ratio from the measured image area and intensity in the second and third images as compared to the baseline image; and computing the aspiration residue volume as the product of the bolus volume and the calculated residue ratio.

4. The method of claim 1 further comprising: if there is significant movement of the patient's head between images two and three, producing separate baseline images for individual comparison with images two and three and calculation of the ratios of pharyngeal and residue volumes to the original bolus volume.

5. Apparatus for quantifying pharyngeal residue of a patient comprising: x-ray imaging means to produce a baseline image of the patient's head and neck; administering an initial volume of x-ray opaque solution to a patient by mouth; x-ray imaging means for imaging the patient having received the solution before swallowing to produce a second image of the head and neck and after swallowing to produce a third image of the head and neck; and means for digitally registering the volume from the second image and the pharyngeal residue volume from the third image; means for digitally registering the volume from the second image and the aspiration residue volume from the third image; calculating means responsive to the digitally registered initial volume and residue for calculating a ratio of the pharyngeal residue volume to the initial volume to determine the proportion of the swallowed bolus that remained in pharyngeal recesses of the patent; calculating means responsive to the digitally registered initial volume and residue for calculating a ratio of the volume of material entering the trachea to the initial volume to determine the proportion of the swallowed bolus that has been aspirated, and calculating the actual pharyngeal residue volume and aspiration volume.

* * * * *